United States Patent [19]

Greenfield et al.

[11] Patent Number: 4,834,711
[45] Date of Patent: May 30, 1989

[54] DISPENSING APPLIANCE FOR INSERTION AND MAINTENANCE OF CATHETERS, TUBES AND OTHER ARTICLES OF THERAPY

[76] Inventors: Albert R. Greenfeld; Jonathan I. Greenfeld, both of 1250 La Venta Dr., Suite 204, Westlake Village, Calif. 91361

[21] Appl. No.: 85,205

[22] Filed: Aug. 14, 1987

[51] Int. Cl.[4] .............................................. A61M 5/00
[52] U.S. Cl. .................................................... 604/172
[58] Field of Search ................... 604/172, 52; 128/767

[56] References Cited

U.S. PATENT DOCUMENTS

| | | | |
|---|---|---|---|
| 3,556,294 | 1/1971 | Walck, III | 604/172 |
| 3,648,704 | 3/1972 | Jackson | 604/172 |
| 3,750,875 | 8/1973 | Juster | 604/172 |
| 3,861,395 | 1/1975 | Taniguchi | 604/172 |
| 3,898,993 | 8/1975 | Taniguchi | 604/172 |
| 4,269,310 | 5/1981 | Uson | 604/172 |
| 4,573,968 | 3/1986 | Parker | 604/52 |
| 4,622,033 | 11/1986 | Taniguchi | 604/172 |
| 4,692,154 | 9/1987 | Singery et al. | 604/172 |

*Primary Examiner*—John D. Yasko
*Attorney, Agent, or Firm*—Ashen Golant Martin & Seldon

[57] ABSTRACT

The appliance lubricates and disinfects the catheter, tube, or other article, as the catheter is inserted into or maintained in a patient's urethra or other body opening. It also mildly anesthetizes the interior of the body opening itself. A contoured shield covers the body site through which the article extends; the shield has flexible stabilizing flaps or a sealing band, or a flange, to fit against the patient's penis or perineum. The catheter is threaded through the conduit, which penetrates the appliance. A reservoir is secured outside or, preferably, inside the appliance. The shield is transparent, and the reservoir contains a conspicuous disinfectant/lubricant/analgesic substance. The reservoir is positioned to provide the user an unobstructed line of sight for ready and accurate positioning of the guide conduit and thus the catheter. Membranes across the conduit retain the substance in the appliance. The membranes are broken at the time of insertion to release the substance into contact with the article and the body passageway. The membranes are broken either by the article itself, as it is threaded through the appliance and inserted into the body, or by manual squeezing of part of the appliance.

35 Claims, 5 Drawing Sheets

DISPENSING APPLIANCE FOR INSERTION AND MAINTENANCE OF CATHETERS, TUBES AND OTHER ARTICLES OF THERAPY

BACKGROUND

1. Field of the Invention

This invention relates generally to appliances for use in medicine, including veterinary medicine; and more particularly to a substance-dispensing appliance for facilitating and enhancing the use of a short-term or indwelling catheter or other tube, or other relatively thin, elongate article employed in therapy.

Various forms of the invention are useful either in insertion or in maintenance—or both—of such an elongate article in a living body. The invention is applicable, for example, to such catheters as the Foley urinary-tract catheter or other urinary catheters, as well as tracheal, cardiac, or other central or other venous catheters.

The invention is also suitable for use with tubes that irrigate or drain body cavities such as (without exclusion) the pleural, peritoneal, subarachnoid, intrathecal, subdural and intracraneal cavities—or that are used for special procedures such as evacuation of hematoma. Furthermore our invention is not limited to use with articles having conductive lumens; rather, it can be employed as well with solid rods—either flexible or stiff—that find therapeutic use in medicine.

For illustrative purposes, we shall first discuss at some length the need for our invention in one familiar area. That is the area of catheters which are placed in the urinary tract.

2. Prior Art

A urinary-tract catheter can be used in hospitalized patients, in elderly patients confined to nursing homes, and in outpatients alike, on both a short- and long-term basis. In any case, catheter insertion is most often accomplished manually by a nurse, doctor, medical student or orderly, under various conditions, often hurried. The catheter is supplied sterile but is subject to contamination anytime after it is removed from its sterile wrap. Major problems with urinary-catheter contamination arise in particular at the time of insertion. For a discussion, see *Cecil's Textbook of Medicine*, seventeenth edition, II:1487, 1985.

Causes of contamination during insertion of a urinary-tract catheter can be multiple. It sometimes happens, for example, that hospital or nursing-home personnel neglect proper aseptic technique and thus transport bacteria, fungus and other infecting organisms from patient to patient.

Improper technique can include failure of medical personnel to wear sterile gloves. Further, medical personnel may unpackage and put on gloves improperly. Personnel also may fail to wear masks on a routine basis, causing contamination of the catheter from the larynx, mouth and nose.

Failure of medical personnel to properly "prepare" (sterilize or drape) a wide enough area of the patient's body can cause contamination if the catheter touches the unsterile area while the catheter is being threaded into the urethral meatus. Contamination can occur during application of aseptic solution to the patient or to the catheter.

A "false passage"—missing the urethral opening during threading—can cause contamination of the catheter on the patient's perineum or anus. A false passage is relatively likely to occur because the catheter is flexible, and therefore difficult to guide into the urethral opening on the first try.

This is especially true for a female patient, whose urethral opening is more difficult to locate than a male's. The insertion process may sometimes have to be started over, thus multiplying the possibilities for contamination and taxing the medical staff member's time, energy and patience.

Problems with catheter contamination are so great, in fact, that urinary-tract catheters are reported to be the major cause of nosocomial (institution-acquired) urinary-tract infections. There is no question that many of these infections could be avoided if catheters could be inserted in a truly aseptic manner.

It has been estimated that 3.6 percent of all patients admitted to hospitals acquire nosocomial urinary-tract infections (Evans, R. Scott, et al., *JAMA*, vol. 256, 1985). Approximately eighty percent of these infections occur in patients who have undergone some form of instrumentation, usually catheterization (see *Cecil's Textbook of Medicine*).

The extra time patients spend in hospitals because of infections related to their short-term and indwelling catheters is estimated at five to six days per hospital stay (see Platt, R. et al., "Mortality associated with nosocomial urinary tract infections," *New Engl. J. Med.* 307:637–642, 1982). The cost of nosocomial urinary-tract infections in hospitals alone is a "staggering 1.8 billion dollars a year" (Rutledge, K. A. and MDonald, H. P., Jr., "The Costs of Treating Simple Nosocomial Urinary Tract Infections," *Supplement to Urology*, vol. 26:24–26, 1985).

Incidence of urinary-tract infection is also high in outpatients who require indwelling urinary catheters, such as paraplegics and people with chronic urinary obstruction. This problem is discussed by Platt, and also by Edwards, C. D., "The epidemiology of 2056 remote site infections," *Ann. Surg.* vol. 184, 1976.

Maintenance of urinary catheters is often necessary for paraplegics, as loss of urinary control commonly accompanies their condition. Heretofore such paraplegics have been maintained on virtually constant antibiotic supply, to avoid urinary infection arising from catheterization; even so, their catheters must be changed on a regular basis.

This technique, however, is unhealthy and undesirable as it carries a danger of both tolerance to existing bacteria and bacterial mutation "around" the available antibiotics. Protracted use of each catheter, with little or no antibiotics, could be enjoyed if there were some way to insert and maintain such catheters free of contamination and infection.

There is little question that urinary-tract infections—many of which can be directly attributed to improper insertion technique—lead to increased costs for medication, doctors' time, longer hospitalization, and increased morbidity and mortality.

In nursing homes, such notorious hazards of urinary-tract infection have apparently deterred the use of urinary catheters on a broad scale, even though such catheters are well known as a means of alleviating the distress of urinary incontinence. Even with such limited use, seven million nosocomial urinary-tract infections—many due to catheter use—occur per year in patients confined to nursing homes (see *Cecil's Textbook of Medicine*).

As a result, elderly patients in nursing homes are generally denied the benefits of such catheters. It is therefore reasonable to consider nursing-home costs arising out of the complications of urinary incontinence. Such costs are estimated in the range $0.5 billion to $1.5 billion per year.

These values represent three to eight percent of all nursing-care costs (see Ouslander, J. G. and Kane, R. L. in "The cost of urinary tract incontinence in nursing homes," *Med. Care* 22:69-79, 1984). Yet, as already suggested, it is generally held that nursing homes would incur greater cost if they put urinary catheters into general use, employing existing catheter-insertion technique.

This discussion makes clear that the need is great for some way to insert and maintain urinary tract catheters, free from the many sources of contamination discussed above. If indwelling urinary-tract catheters could be inserted aseptically—and particularly if they could be maintained free of contamination and infection for long periods after insertion—the favorable results would include great reductions in infection and human suffering, and save millions of dollars in time and costs every year.

The need is not limited to urinary catheters. A like need exists whenever sterile catheters, tubes, or other elongate articles of therapy are inserted under sterile conditions into a living body. Examples include (among others) pacemakers and central lines (catheters or tubes placed into large veins), as well as Swan-Ganz catheters.

Often these must be inserted under emergency conditions in emergency rooms and intensive- and cardiac-care units. In these situations sterility is too easily compromised.

Our discussion to this point has focused on the medically crucial considerations of contamination and infection. Yet there are other parallel concerns in the use of catheters and other therapeutic inserts, particularly those articles that are fitted closely into a very narrow preexisting bodily duct such as the male urethra.

Such concerns saliently include friction and pain. Urinary catheterization of male patients may be among the most greatly feared of routine medical procedures.

Although a portion of this response may arise from the special psychological considerations associated with the reproductive organs, nonetheless these organs are extremely sensitive. Insertion is often mechanically difficult and sometimes extremely painful.

There is accordingly an important need to reduce the mechanical friction of insertion, and with it a great deal of discomfort. In addition there is a need to desensitize the affected internal membranes to the residual trauma of insertion.

SUMMARY OF THE DISCLOSURE

Our invention is addressed to all three of these problems—contamination, friction and pain—that arise in use of catherers, other tubes, and therapeutic elongate inserts generally. The invention is a dispensing appliance for use with a therapeutic thin elongate article that extends into a living body at a site on the body (not necessarily an external site).

By "thin" we mean only that the article is substantially thinner than it is long. Our invention can be used with therapeutic articles as large as one centimeter in diameter, and even larger.

This appliance is for use with a reservoir containing a substance, and is used to dispense such a substance from the reservoir. Substances of particular interest include disinfectant, lubricant, and anesthetic or analgesic preparations. The appliance may be used to dispense a substance that includes any one or any combination of such preparations.

In use, the invention applies the substance to the thin elongate article and thereby to the living body. In some cases the substance is thereby dispensed into a body passageway in which the article is positioned; in some cases the substance is dispensed onto the external body area at the site through which the article extends into the body; in some cases both may occur.

The appliance includes a shield for covering the site and the area of the body immediately surrounding it. The appliance also includes a conduit defined through the shield. The conduit is particularly sized for receiving and surrounding a portion of the thin elongate article, outside the body, for purposes to be described.

In addition, the appliance includes some means for securing the substance reservoir to the shield. For purposes of broad generality in expressing our invention, we shall call these means the "securing means."

The appliance also includes some means for conveying the substance from the reservoir to the conduit. Again for generality we shall call these means the "conveying means."

In use, by virtue of this structure, substance from the reservoir is present within the conduit. In the conduit the substance is applied to the thin elongate article, and thereby to the body.

The foregoing description may provide a definition of our invention in its broadest forms. We prefer, however, to incorporate certain additional characteristics or features to optimize enjoyment of the several benefits of the invention.

For example, some forms of the invention are used in insertion of the thin elongate article into the body. Thus in such forms of the invention the "site" mentioned earlier is an insertion site, and the conduit is a guide conduit for guiding the article to the insertion site.

Some forms of the invention include the reservoir itself, secured to the shield. In some of such forms the reservoir may be secured within the shield, and in fact may be formed within and by the material of which the shield is composed.

Some forms of the invention also include some means for retaining substance in the appliance before use. These means—again, the "retaining means"—are adapted and disposed to be opened at insertion of such article through the guide conduit.

By the phrase "at insertion" we mean to encompass two different groups of forms of our invention. In one group, the retaining means are mechanically opened by the process or act of insertion itself. In other forms, the retaining means are opened by some other mechanical agency at generally the same time as insertion occurs.

In any event, before use the retaining means in some forms of our invention retain the substance within the reservoir. In other forms of our invention before use the retaining means do not necessarily confine the substance to the reservoir; rather the retaining means may be structured so that the substance also is present in the conduit, in the conveying means, or in other parts of the appliance, or in combinations of such locations.

One embodiment of our invention—which may overlap some forms already discussed—is particularly for use in insertion of a catheter into a urethral meatus. In some variants of this embodiment of our invention, the reservoir is a separate dispensing reservoir that is not part of the appliance, though the previously mentioned securing means are part of the appliance.

In this embodiment of the invention, the shield is particularly configured for covering the urethral meatus and the area of the body immediately surrounding it. The shield may be particularly contoured and adapted to maintain itself stably in place upon the areas adjacent to the meatus. The conduit is particularly sized and adapted for guiding the catheter to the meatus.

In a variant having no reservoir as part of the appliance, the reservoir may be present in the form of a common supply container—a squeeze bottle, for example, or an elevated reservoir with a gravity-fed supply tube. This variant of the invention also includes a duct or ducts disposed and connected to convey the substance from the securing means to the conduit.

Another embodiment of our invention, which also may overlap the embodiments or forms already discussed, has some means for projecting the substance from the reservoir along the article. These "projecting means," typically within the shield, project the substance along the article, through the site and into the patient's body.

In this embodiment the conveying means may include a duct, for providing substance communication between the reservoir and the conduit; and the projecting means may include an outlet for the duct. This outlet directs the substance from the reservoir at a selected angle and position to the article within the conduit.

In effect, the outlet functions as a nozzle to squirt the substance at the article in a preselected way. This arrangement facilitates continuing movement of the substance along the article out of the shield and into the body.

This form of our invention is advantageously combined with an elongate article that has some means for conducting the substance lengthwise along at least a part of the article. Such "conducting means" may include, for example, a groove formed in an exterior surface of the article, for distribution of the substance along the article to the interior of the body. At any rate the projecting means and conducting means are mutually configured for effective transfer of the substance from the reservoir into the body.

We prefer to provide the article with generally spiral external grooving, to conduct the substance from the dispensing appliance through the site and into the body. Through this arrangement the effective distribution of the substance, relative to the passageway within the patient's body, is not only axial but also circumferential.

In some of these forms of the invention, if the reservoir is within the shield, the conduit may open directly into the reservoir at proximal and distal sides of the shield (i.e., at proximal and distal ends of the reservoir). In this configuration, the article passes directly through the reservoir.

At the other extreme, the reservoir in these forms of the invention may be a separate dispensing container that is not part of the appliance at all—as noted earlier. Intermediate forms of the invention include the reservoir, either as a discrete structure outside the shield, or in the shield but to some extent distinct from the conduit.

All these forms of the invention have their own purposes and limitations, as will be detailed shortly.

In the use of our invention at the time of insertion generally, when the flexible urinary-tract catheter or other tube or article passes into the opening of the appliance, the catheter comes into contact with a substance (lubricant, disinfectant and/or analgesic solution), and remains in such contact along the entire length of the conduit. The disinfectant if included enhances sterility, beyond that provided by the original sterile wrap of the catheter package.

Thus our appliance sterilizes the catheter as the catheter is inserted. It also compensates for various human errors that can cause contamination.

Overall, the chance of a contaminating false passage is greatly reduced. First, the insertion route is essentially fixed before he catheter reaches the patient. Secondly, a small misalignment can be corrected by a fine last-minute adjustment without contamination, since the appliance, catheter and area are bathed in antiseptic.

Bathing the catheter in lubricating solution as it is guided into the patient's body also has the effect of lubricating the catheter and thus facilitating entry into the body. Entry of an extremely flexible catheter is also facilitated by the rigidity of the appliance itself.

(Since the invention may be used in veterinary as well as human medicine, the term "patient" is to be understood to encompass animal as well as human patients.)

Including analgesic or anesthetic in the substance also has the effect of applying such analgesic or anesthetic to the patient's tissues within the body. This application is intended to reduce the pain of insertion.

The invention is not limited, however, to use at the time of insertion. Various forms, as will be clear from discussions in this document, are suited for use in maintaining a therapeutic insert that is already present—to reduce or eliminate infection, friction arising in natural shifting of the insert in the body, and pain.

All of the foregoing operational principles and advantages of the present invention will be more fully appreciated upon consideration of the following detailed description, with reference to the appended drawings, of which:

DETAILED DESCRIPTION OF THE PREFERRED EMBODIMENTS

Figure 1:
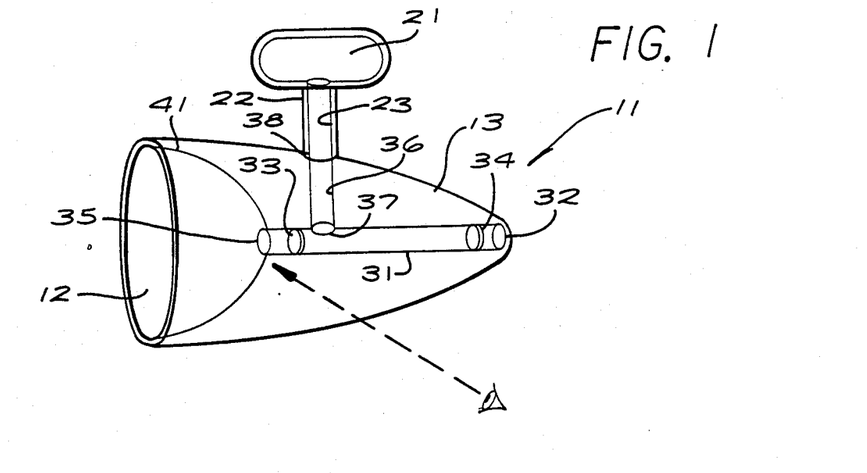
FIG. 1 is a side and rear isometric view of a preferred embodiment of the invention, incorporating an exterior reservoir and a guide conduit, and employing membranes as retaining means.

A preferred embodiment of our invention, shown in FIG. 1, includes a shield 11 that has two sides. One side 12 faces toward the patient's body, and one side 13 faces away from the patient's body, toward the user. The shield also has a generally central portion 14.

This embodiment has hollow exterior reservoir 21 designed to contain an antiseptic, lubricant, and/or analgesic substance that bathes the catheter before and during its insertion into the human body. This reservoir 21 communicates with the lumen 23 of a tube 22, which is in turn secured to the shield 11. The lumen 23 within the tube 22 is made continuous at junction 38 with a bore 36 that passes partway through the shield 11 to join the guide conduit 31 at junction 37.

The guide conduit 31 has two ends which communicate with the two ends of the appliance, one proximal and one distal to the patient, at 35 and 32, respectively. The diameter of the guide conduit may be tailored to the gauge of the catheter to be used.

Inside the hollow guide conduit there are two membranes 34 and 33, respectively, which the catheter must penetrate to enter and leave the conduit respectively. Breaking membrane 34 with the flexible tip of the catheter itself brings the catheter into contact with the substance.

This preferred embodiment of our invention also is equipped with a ridge or flange 41. The flange is provided to help steady the appliance against the patient's body, and is designed for the size and gender of the patient. That is, the flange cups the male's penis or sets off the female's meatus from the surrounding perineal area.

The junction 37 or 38 may instead be occluded by a membrane which can be broken by gentle pressure (such as squeezing by the hand of the person inserting the catheter) to introduce the substance into the guide conduit.

Alternatively, an exterior clamping device or a rotary valve or other closure mechanism (not illustrated), may be provided on the tube 22. Release of the clamp will cause the substance to flow into the guide conduit. In any event, as the catheter is inserted it is resterilized or lubricated, or both; and the passageway in the patient's body is sterilized, lubricated or partially anesthetized, or combinations of all three.

Variants of the FIG. 1 embodiment are within the scope of our invention. For example, the membranes 33 and 34 may be placed at the openings 32 and 35 of the appliance; or they may be omitted entirely, and other means employed to retain the substance within the appliance.

In its preferred embodiments, our invention is transparent—as indicated in the accompanying illustrations. If desired for special applications, the appliance can be made translucent or even opaque.

We prefer transparency, however, as it allows the user to see clearly the guide conduit and the patient's meatus, and thereby to position the conduit correctly relative to the meatus. The line of sight 61 represents an angle of vision which should provide the user with an advantageous view of the insertion site.

To further aid correct emplacement of the appliance at the opening into which the catheter is to be inserted, the lubricant and disinfectant may be a brightly colored solution Such coloration helps to make the guide conduit, and particularly the end of the guide conduit set against the patient's body, easily viewed by the person inserting the catheter.

Figure 2:
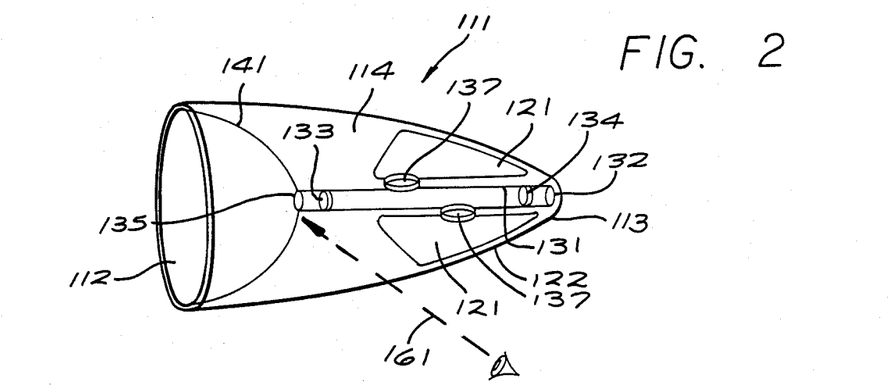
FIG. 2 is a like view of another preferred embodiment of our invention, also using a guide conduit and using membranes, but in which the reservoir is inside the appliance.

Another preferred embodiment of our invention, shown in FIG. 2, comprises a like shield 111 with generally two faces and a central body area (112, 113, 114).

Reference numbers in FIG. 2 and in the five figures following have been selected so that corresponding parts have corresponding numbers in different embodiments, each within a different "100-series". Thus item 12 corresponds to 112 in another embodiment, and to 212 for example in yet a third embodiment.

The FIG. 2 embodiment has an internal cavity 121, which serves as an internal reservoir for the substance that will bathe the catheter as it passes into the patient's body. This internal reservoir 121 is preferably disposed in the distal half or two-thirds of the shield 111.

In other words, the reservoir is set well forward from the proximal end of the appliance, which cups the patient's anatomy at catheter insertion. This internal positioning is important as it helps a user to see clearly what he or she is doing, during alignment of the guide conduit and the catheter with the patient's urethral meatus.

The reservoir wall 122 is relatively thin near the distal end of the shield 111, but is formed by the bulk 114 of the shield 111 at the proximal end. The reservoir 121 completely encircles the guide conduit, and communicates with the conduit via one or more holes 137.

Since the reservoir has been positioned forward and away from the proximal end of the appliance, the reservoir does not obstruct the natural line of vision (sight line 161) along which the user will view the end of the guide conduit in its approach to the meatus.

Alternatively, the internal reservoir—instead of substantially filling the distal interior of the appliance—may be two or more chambers inside the appliance.

At insertion, the catheter pierces a distal membrane 134 to enter the guide conduit and the substance bath. The catheter then also pierces a corresponding proximal membrane 135, to enter the meatus—releasing some of the substance onto at least the external body surfaces surrounding the meatus.

(If preferred, the appliance may be configured so that squeezing of the appliance from the outside, as by one hand of the person inserting the catheter, will suffice to release the substance into the guide conduit to bathe the catheter.)

The catheter also carries some of the substance into the patient's urethra to reduce the bacterial population near the distal segments of the urethra, or to lubricate or anesthetize the urethra, or to perform any combinations of these three functions. The configuration of the reservoir as well as the amount of liquid contained in the appliance are calculated to effectively perform these functions without excess spillage onto the perineal area of the patient's body.

The membranes 134, 135 form a barrier system that serves to maintain sterility of the interior of the guide conduit as well as to retain the substance within the appliance before use.

Figure 3:
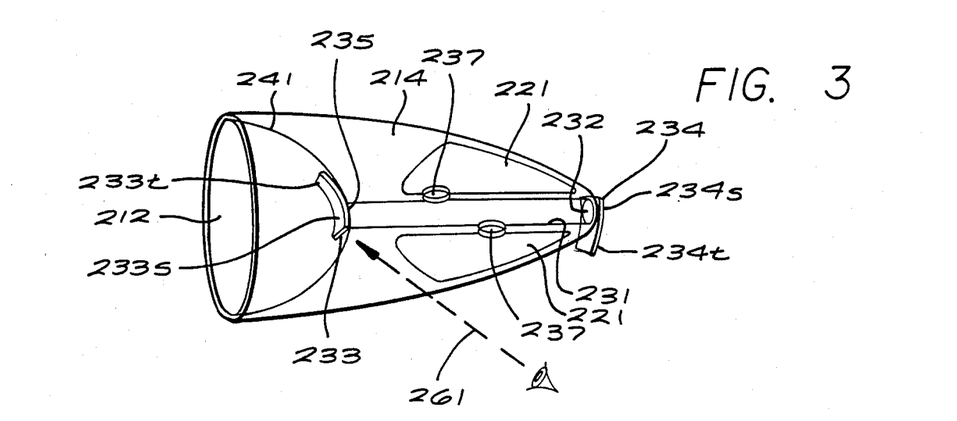
FIG. 3 is a like view of a similar embodiment of the invention employing pull tabs to retain the substance.

It is also possible, as shown in FIG. 3, to use substance-retaining means consisting of two exterior pull-tab seals 233 and 234, both easily accessible to the user at the two ends of the appliance.

The pull-tab seals include sealing portions 233s, 234s, located at the patient and user ends of the appliance, respectively, which retain the substance inside the appliance. The pull-tab seals also include tab segments 233t, 234t designed to be pulled by the user to remove the seals from the appliance. After such removal, the catheter can enter and the substance can flow toward the patient.

Figure 4:
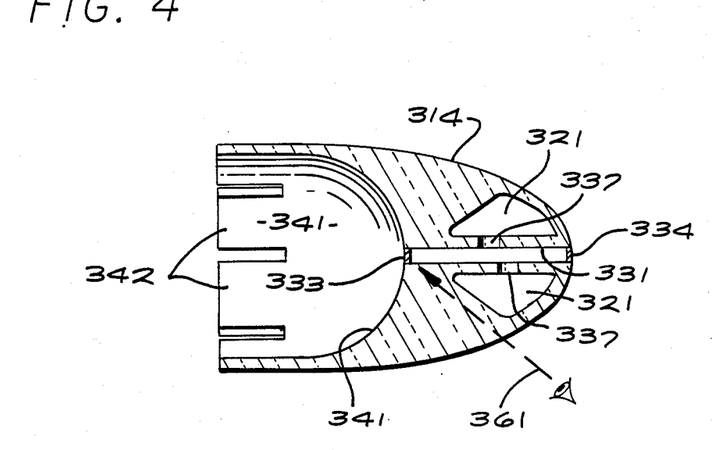
FIG. 4 is an elevation in longitudinal section of an embodiment related to the FIG. 2 embodiment, but having a multifurcated flexible flange to help steady the appliance against the body of a male patient.

Different embodiments of our appliance may incorporate different flange configurations for positioning against the patient's body, as at 41, 141 and 241 in FIGS. 1 through 3 respectively. In the embodiment of FIG. 4, the flange 341 is multifurcated to form several flexible flaps 342 along the proximal edge of the flange 341. These allow the appliance to be stably positioned upon a patient's penis.

The reservoir 321, again, is positioned forward in the shield 314 to allow the user a clear sight line 361 to the proximal end of the guide conduit, with its membrane 333.

Figure 5:
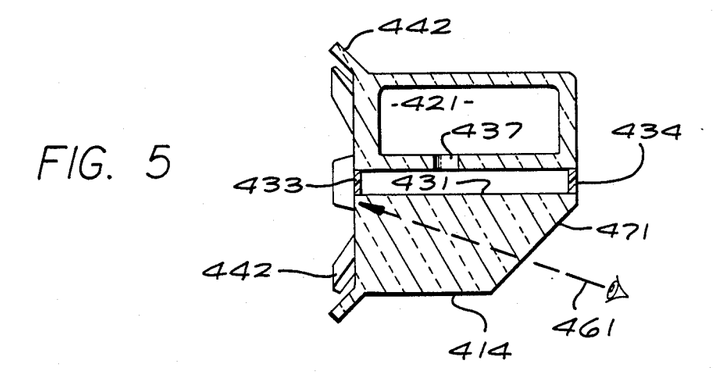
FIG. 5 is a similar view of a related embodiment that has a shaped flange to help stabilize the appliance against a female patient's body.
Figure 6:
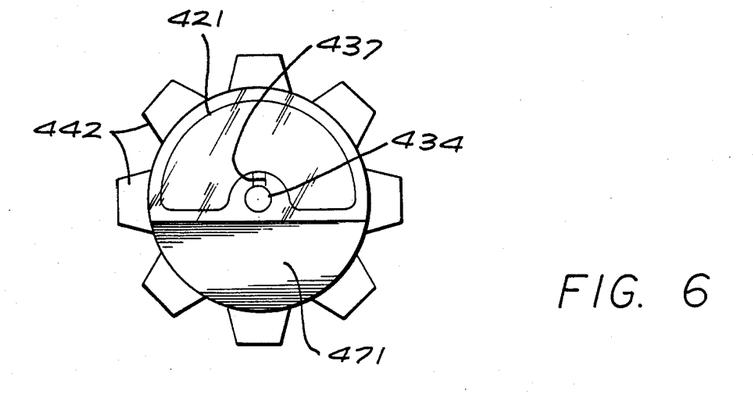
FIG. 6 is an elevation, taken from the user s or distal side, of the FIG. 5 embodiment.

In the embodiment of FIGS. 5 and 6, the flanges 442 are quite short, for stabilization against a female patient's perineal area surrounding the meatus.

In this embodiment of our invention, as the female meatus is often difficult to locate, the sight line 461 through the shield should offer a clear view of the proximal end of the guide conduit 431 and exit membrane 433 relative to the patient's meatus. To this end, one side 471 of the appliance is cut away and flattened so that the user's view is not distorted by curvature of the shield.

Figures 7, 8, 9, 10:
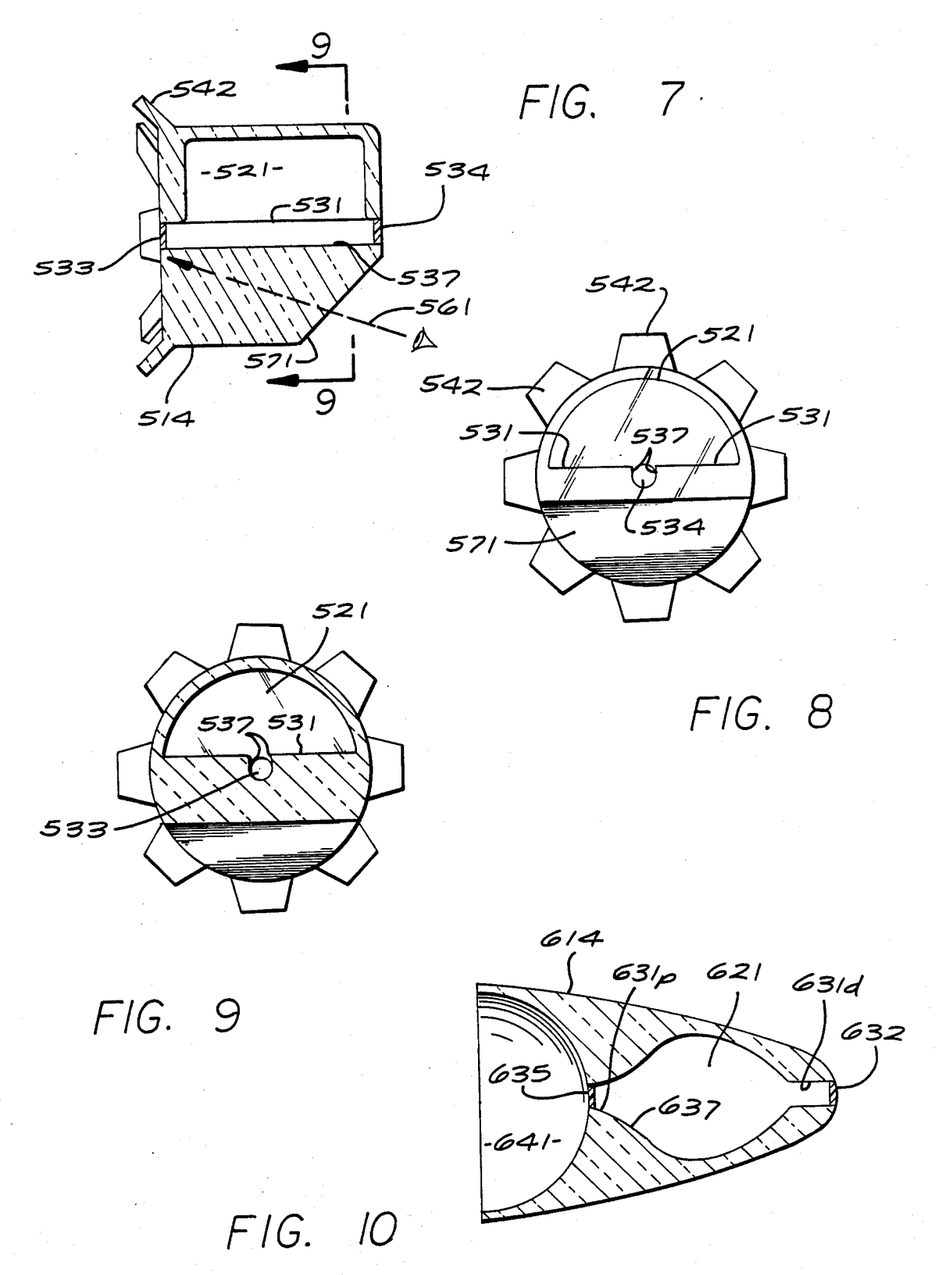
FIG. 7 is an elevation in longitudinal section of an embodiment much like that of FIGS. 5 and 6, but having a guide groove instead of a guide conduit.
FIG. 8 is an elevation, taken from the distal said, of the FIG. 7 embodiment.
FIG. 9 is a cross-sectional elevation of the same embodiment, taken along the lines 9—9 of FIG. 7.
FIG. 10 is an elevation in longitudinal section of an embodiment similar to that of FIGS. 2 through 4, but having an in-line reservoir rather than a distinct guide conduit formed through the reservoir.

A related embodiment appears in FIGS. 7 through 9. Here instead of a guide conduit, distinctly separated from the guide reservoir by a structural wall 131, . . . 431 as in the previously discussed drawings, there is provided a guide trough or groove 537 along the bottom wall or base 531 of the reservoir 521.

The bottom wall 531 of the reservoir 521 thus forms a ledge 531—appearing in FIG. 7 as an uninterrupted horizontal line 531—at the top of the trough 537. In the distal end view of FIG. 8 these features are visible through the transparent end face of the appliance. The circular distal membrane 534 also appears in FIG. 8. In FIG. 9 the corresponding circle 533 represents the proximal membrane 533, visible at the far end of the trough 537.

FIGS. 1 through 6 illustrate a reservoir that is entirely distinct from the guide conduit, and FIGS. 7 through 9 show a reservoir with a partially distinct guide trough. FIG. 10, by contrast, shows a reservoir into which the guiding function is almost entirely absorbed.

At the distal side of the shield, just inside the distal membrane 632, the distal end 631d of the guide conduit opens directly into the reservoir 621. The reservoir 621 is accordingly "in line" with the guide conduit. If desired, the distal end 631d of the conduit (i. e., the distal restriction of the reservoir) may be eliminated completely.

At the proximal side of the shield, just inside the proximal membrane 635, the proximal end 631p of the guide conduit likewise opens directly into the reservoir 621. Here, however, if the appliance is intended for use with a therapeutic article that is at all flexible, it appears desirable to form the proximal end 637 of the reservoir wall into a funnel shape as illustrated.

In use, a flexible article may droop slightly in passage through the reservoir and therefore fail to align with the proximal membrane 635. This problem is avoided by provision of the funnel section 637, to guide the proximal end of the therapeutic article back onto center.

Figures 11, 12:
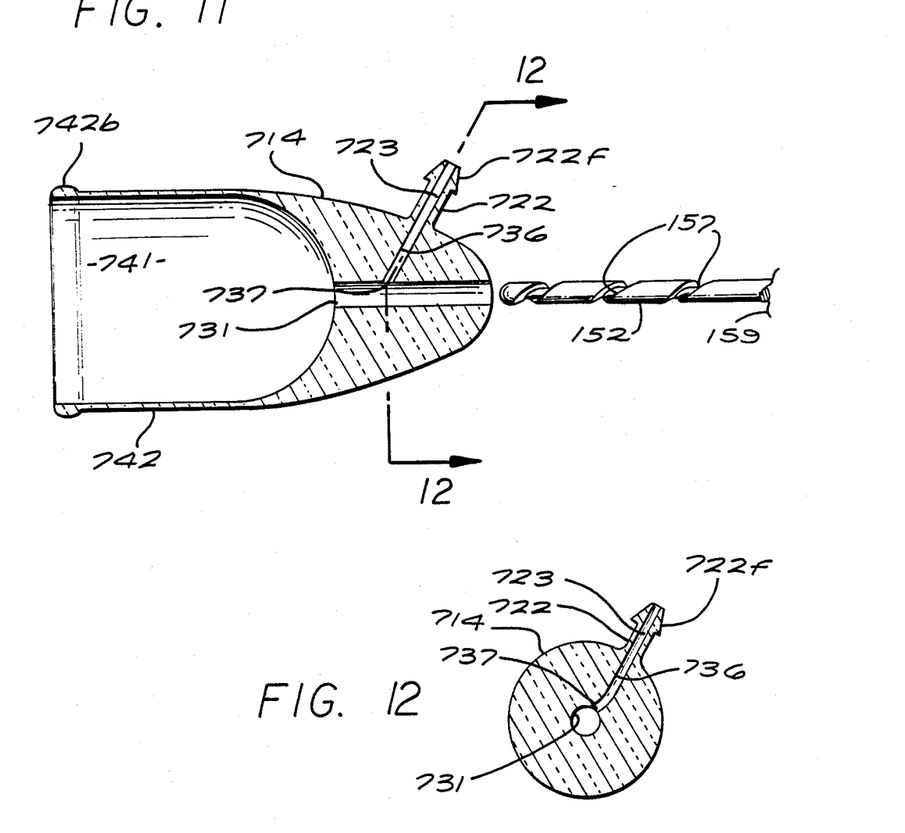
FIG. 11 is a like view of another embodiment that is similar, but in which the proximal flange is extended into a sealing skirt, the internal reservoir and membranes are entirely omitted in favor of a substance-projection duct that attaches to a separate external reservoir, and a spirally grooved therapeutic article is provided in combination.
FIG. 12 is a cross-sectional elevation of the same embodiment, taken looking distally along the lines 12—12 of FIG. 11.

The article is thereby repositioned to puncture the proximal membrane 635, for entry into the urethral meatus. FIG. 11 shows that the proximal end of the appliance may be extended as at 742 into a very thin, flexible membrane 742b, to sealingly grip the patient's penis—as does the proximal end of a rubber prophylactic.

This feature is advantageously combined with separation of the reservoir entirely from the appliance. It is possible to design embodiments of our appliance, for both male and female patients, so that the disinfectant is introduced into the appliance from an entirely separate device.

Such a device may take the form of a common reservoir that serves, for example, a complete wing of a hospital or an entire nursing home. Such a supply system may have supply lines running through the walls, and may be either gravity fed or pressurized. If preferred the reservoir may instead be a small commercial dispenser container such as a squeeze bottle, or even a bulb syringe. Any of these may be attached temporarily onto the appliance during use, after separate shipment and storage.

Thus in FIGS. 11 and 12 a duct 736, communicating with the guide conduit 731, is extended as at 723 through a nipple 722 external to the shield proper 714. The nipple may terminate in a hose fitting 722f.

At its proximal end the duct 736 terminates in a shaped outlet 737—which is angled axially toward the proximal end of the guide conduit. Further, as is particularly clear in FIG. 12, the outlet 737 enters the guide conduit 731 generally on a tangent to the periphery of the conduit.

Due to this axial and tangential orientation of the outlet 737, in use the substance received from the separate reservoir through the duct 723, 736 is projected into the conduit 731 in a helical, swirling trajectory toward the patient's urethra. Preferably the catheter or other elongate article 152 (drawn cut off as at 159 for convenience of scale) is correspondingly formed with a generally helical shallow external groove or depression 157.

The article 152 can be inserted into the shield just far enough so that one of the spirals of this grooving is aligned with the duct outlet 737 inside the conduit 731. When that is done, in use the substance received through the duct 723, 736 is projected along the grooving 157 toward the insertion site (not shown) at the urethral meatus. If the article 152 is inserted into the urethra, or just short of being so inserted, the substance is thus projected along the article 152 into the urethra.

Before the article 152 is actually fully inserted into the urethra, this configuration can be used to propel the substance into the urethra in advance of the therapeutic article 152. This technique serves to disinfect, lubricate, and/or anesthetize the urethra.

After the article 152 is fully inserted (as, for example, into the urinary bladder), the same configuration can be used to flush the urethra periodically with the substance. The result is to maintain the urethra relatively free of contamination and thereby of infection—and also to minimize friction and/or pain due to normal shifting of the body.

As previously mentioned, the thin rubber sealing section 742 (FIG. 11) is advantageously combined with this conduction of the substance into the urethra as by generally spiral grooving 157. We consider this combination advantageous because the sealing provision 742, 742b deters the proximally projected substance from leaking into the patient's clothing or bedclothes.

It must also be noted, however, that the sealing section 742, 742b and the spiral projection arrangement—as well as the separate, discrete reservoir connected to the appliance only by a hose fitting 722f—are all three separate and distinct features of our invention. Accordingly they need not all be provided together, but rather may be provided either individually or in any combination for such beneficial purposes as may appear.

Figure 13:
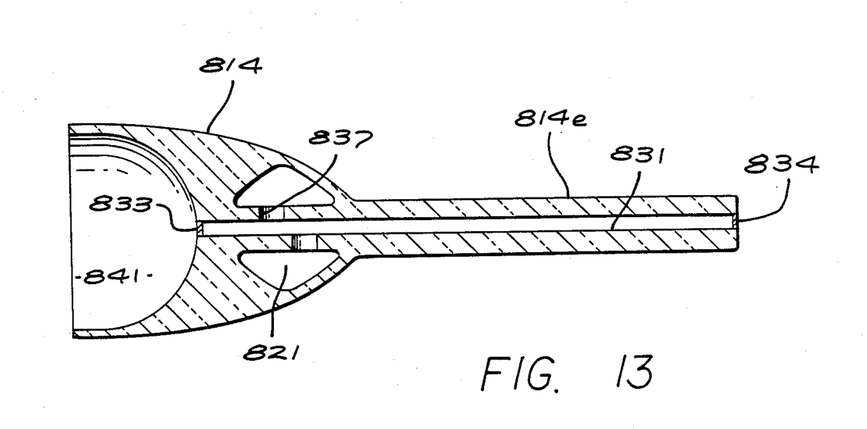
FIG. 13 is an elevation in longitudinal section of yet another embodiment similar to that of FIGS. 2 through 4, but having a distally elongated extension.

As shown in FIG. 13, the forward or distal side of the shield may be formed into an extension 814e if desired to provide a longer alignment path or simply a better manual grip surface. The reservoir 821, if present, may be within the shield 814 proper as illustrated—or if preferred may be formed at some location (not shown) partway out the distal extension 814e, or even at its distal tip near the distal membrane 834.

Figure 14:
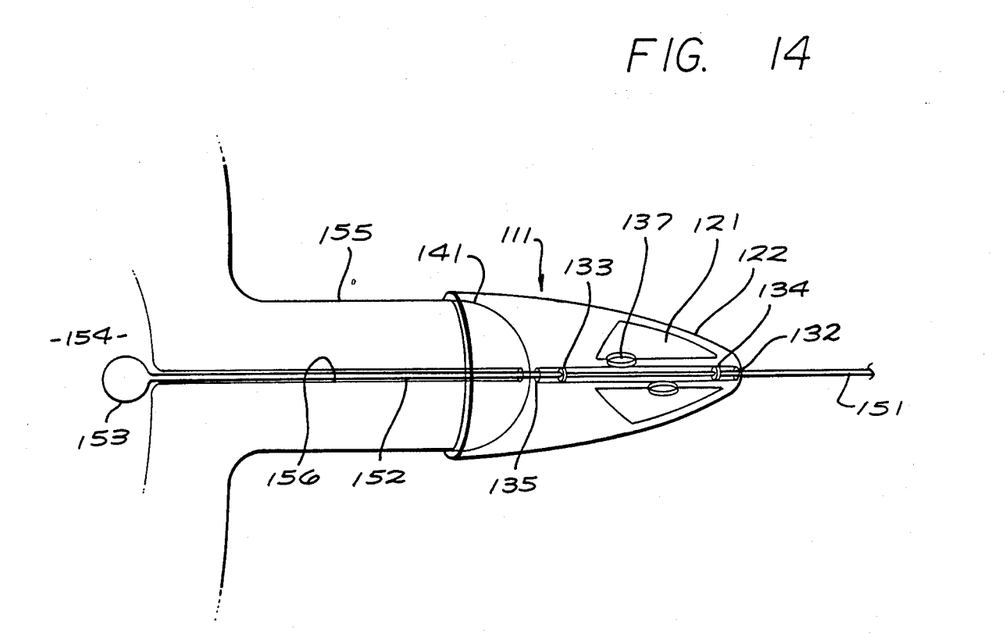
FIG. 14 is a somewhat schematic view of the FIG. 2 embodiment in use, guiding a catheter through the urethra into the patient's bladder.

FIG. 14 shows the appliance 111 in place cupped over a male patient's penis 155, with a balloon catheter 151-153 inserted past the reservoir 121 and the proximal or exiting membrane 133, through the urethra 156 and into the urinary bladder 154.

Figure 15:
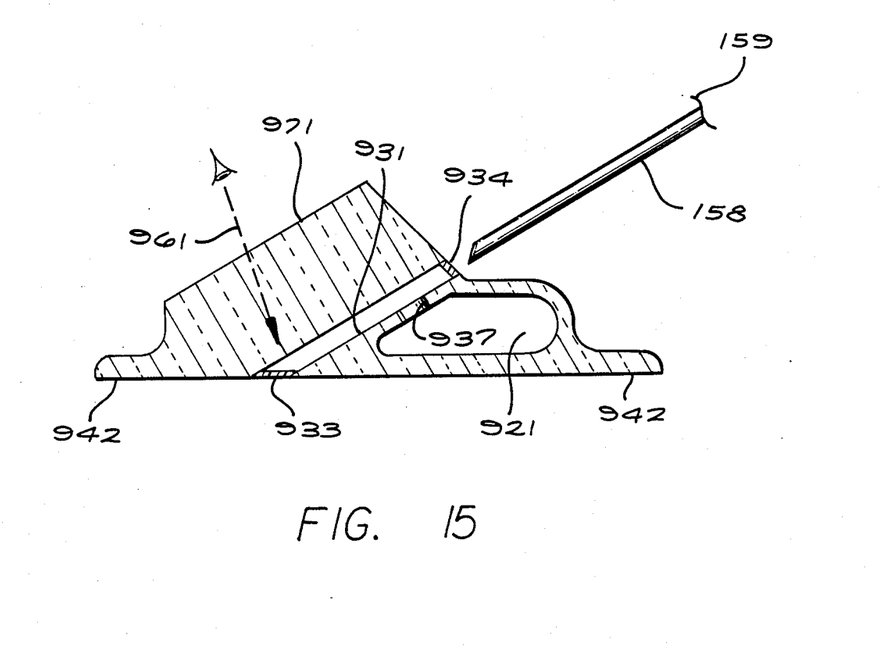
FIG. 15 is another embodiment for use with therapeutic articles such as sharpened hollow needles.

Another embodiment of our invention, particularly adapted for use with therapeutic articles such as sharpened hollow needles 158, appears in FIG. 15. Here the guide conduit 931 is of correspondingly narrower bore, and angled very shallowly in relation to the base 942.

By virtue of this shallow guide-conduit angle, the needle 158 (drawn cut off as at 159 for convenience of the illustration) will enter the patient's body at a correspondingly shallow angle. It is thus oriented to intercept a blood vessel or the like at an acute angle as is customary for optimum accuracy.

The embodiment of FIG. 15 may be provided with a reservoir that is either internal but distinct from the guide conduit 931, as illustrated at 921; or offset with a groove as in FIGS. 7 through 9, or in-line as in FIG. 10, or separate from the appliance as suggested in FIGS. 11 and 12. Thus it will be seen again that these various features may be used generally independently as suited for purposes at hand. A planar viewing port 971 may be included.

The substance dispensed through our appliance may take any of a very great variety of forms. We see it as likely that special preparations will be developed to enhance and optimize the benefits of our invention. Of course all such substance forms are within the scope of our invention. By way of fully disclosing the practice of the invention, however, for urinary-catheter uses our invention contemplates a substance with these commercially available preparations:

as antiseptic, povidone-iodine, roughly ten percent;
as lubricant, sterile surgical lubricating jelly; and
as analgesic, two-percent lidocaine.

Proportions may be varied as appropriate. A suitable substance would be sixty-five percent of the above-stated antiseptic, twenty percent of the lubricant, and fifteen percent analgesic. The antiseptic and analgesic are preferably dissolved in a water-soluble lubricant. As antiseptic for example, one preparation now available commercially for use in treating vaginal irritations is ten-percent povidone-iodine in antiseptic gel. In view of its intended use, such a material may be expected to produce only minimal irritation of mucous membranes.

It will be understood that the foregoing disclosure is intended to be merely exemplary, and not to limit the scope of the invention—which is to be determined by reference to the appended claims.

We claim:

1. A dispensing appliance for use in insertion of a therapeutic thin elongate article that extends into a living body at an insertion site on the body; said appliance comprising:
    a shield for covering such site and immediately surrounding area;
    a guide conduit, defined through the shield, for receiving and surrounding a portion of such thin elongate article outside the body and for guiding such article to such insertion site;
    a reservoir containing a substance;
    means, connected with the substance reservoir and with the shield, for securing such substance reservoir to the shield;
    means, connected with the substance reservoir and with the shield, for conveying such substance from such reservoir to the conduit; and
    means, opened at insertion of such article through the guide conduit, for retaining substance in the appliance before use of the appliance;
    whereby substance from such reservoir is applied to such thin elongate article and thereby to such body; and wherein:
    the shield defines a first side that faces such body during use, and a second side that faces away from such body during use; and
    the retaining means comprise at least two membranes, one for deterring flow of substance in the guide conduit toward the first side of the shield, and another for deterring flow of substance in the guide conduit toward the second side of the shield.

2. The appliance of claim 1, wherein:
    the retaining means comprise means for retaining substance in the reservoir before use of the appliance.

3. The appliance of claim 1, wherein:
    the retaining means comprise at least one frangible membrane that is broken by such thin elongate article upon insertion thereof.

4. The appliance of claim 1, wherein:
    the retaining means comprise means for preserving sanitation within the guide conduit before use of the appliance.

5. A dispensing appliance for use in insertion of a therapeutic thin elongate article that extends into a living body at an insertion site on the body; said appliance comprising:
- a shield for covering such site and immediately surrounding area;
- a guide conduit, defined through the shield, for receiving and surrounding a portion of such thin elongate article outside the body and for guiding such article to such insertion site;
- a reservoir containing a substance;
- means, connected with the substance reservoir and with the shield, for securing such substance reservoir to the shield;
- means, connected with the substance reservoir and with the shield, for conveying such substance from such reservoir to the conduit; and
- means, opened at insertion of such article through the guide conduit, for retaining substance in the appliance before use of the appliance and for preserving sanitation within the guide conduit before use of the appliance;
- whereby substance from such reservoir is applied to such thin elongate article and thereby to such body; and wherein:
- the shield defines a first side that faces such body during use, and a second side that faces away from such body during use; and
- the retaining means comprise at least two membranes, one disposed across the guide conduit substantially at the first side of the shield, and another disposed across the guide conduit substantially at the second side of the shield.

6. The appliance of claim 1, particularly for use in insertion of such an elongate article into a urethral meatus, and wherein:
- the shield is shape as the complement of surfaces adjacent such urethra; and
- the substance is a disinfectant.

7. The appliance of claim 1 wherein:
the shield is generally transparent.

8. The appliance of claim 1:
- wherein the shield is generally transparent; and
- further comprising means for rendering distinctly conspicuous the position of the guide conduit at said first side of the shield, as viewed from the second side.

9. The appliance of claim 8, further comprising:
- a quantity of distinctly colored substance within the reservoir, and within at least a portion of the guide conduit near the first side of the shield;
- whereby the position of the guide conduit within the appliance is made distinctly conspicuous by the coloration of the substance therein.

10. The appliance of claim 1, wherein:
the reservoir is secured within the shield.

11. The appliance of claim 1, wherein:
the substance is a lubricant.

12. The appliance of claim 1, wherein:
the substance is an analgesic.

13. The appliance of claim 1, wherein:
the substance is a lubricant and analgesic.

14. The appliance of claim 1, wherein:
the substance is a lubricant and disinfectant.

15. The appliance of claim 1, wherein:
the substance is a lubricant, analgesic and disinfectant.

16. The appliance of claim 10, wherein:
the shield is generally transparent; and
the shape and placement of the reservoir permit substantially clear viewing of the guide conduit at and near a side of the shield that faces such body during use.

17. The appliance of claim 1, particularly for use in insertion of a catheter into a urethral meatus; and for use with a substance that is a disinfectant or lubricant or analgesic, or any combination of two or more of these types of substance; and wherein:
- such reservoir is a separate dispensing reservoir that is not part of the appliance;
- the shield in use covers such meatus and immediately surrounding area, and is stably placed and retained upon surfaces adjacent such meatus;
- the conduit guides such catheter to such meatus; and
- the conveying means comprise a duct disposed and connected to convey such substance from the securing means to the conduit.

18. The dispensing appliance of claim 1, further comprising:
- means, within the shield, for projecting such substance from the reservoir along such article, through such site and into such living body.

19. The appliance of claim 18, wherein:
- the conveying means comprise a duct providing substance communication between the reservoir and the conduit; and
- the projecting means comprise an outlet for the duct, within the shield, for directing such substance from the reservoir at a selected angle and position to such article within the conduit.

20. The appliance of claim 18, wherein:
- at proximal and distal sides of the shield, the conduit opens directly into the reservoir;
- whereby such article passes directly through the reservoir.

21. The appliance of claim 18:
- in further combination with such a thin elongate article that has means for conducting such substance lengthwise along at least a part of the elongate article.

22. The appliance of claim 21, wherein:
- the conducting means comprise at least one groove formed in an exterior surface of the elongate article, for distribution of such substance to the interior of such living body.

23. The appliance of claim 22, wherein:
- the conducting means comprise at least one internal passage within the elongate article, communicating with an exterior surface of the elongate article for distribution of such substance to the interior of such living body.

24. The appliance of claim 21, wherein:
- the projecting means and conducting means comprise means for effectively transferring such substance from the reservoir into such living body along the elongate article.

25. In combination, the appliance of claim 1, together with:
- such thin elongate therapeutic article;
- the article having generally spiral external grooving for conducting such substance from the dispensing appliance through such site and into such living body; and
- wherein the conveying means comprise a duct within the shield, having an outlet that is disposed and angled consistently with the grooving of the elongate article when the article is positioned in the conduit and extends into such living body;

whereby the duct and its outlet project such substance from the reservoir into and along the grooving, through such site and into such living body.

26. The appliance of claim 18, particularly for use in inserting or maintaining such thin elongate article within a urethra, such site being a urethral meatus; wherein:

the conduit is particularly sized to match a urethra;

whereby the conduit closely surrounds and encloses such thin elongate article that fits closely within such urethra; and whereby in use such substance is effectively applied along at least a part of the length of such urethra while such thin elongate article is positioned within such urethra.

27. The appliance of claim 25, particularly for use in inserting or maintaining the thin elongate article within a urethra, such site being a urethral meatus; wherein:

the conduit is particularly sized to match a urethra; and the article is particularly sized to fit closely within such urethra;

whereby in use such substance is effectively applied along at least a part of the length of such urethra while the thin elongate article is positioned within such urethra.

28. The dispensing appliance of claim 1, for use with such reservoir in the form of a separate dispensing reservoir that is not part of the appliance and that contains a substance which is a disinfectant or lubricant or analgesic, or any combination of two or more of these types of substance; wherein:

the conveying means comprise a duct for conveying such substance from the securing means to the conduit; and the appliance further comprises means, within the shield, for projecting such substance from such reservoir along such article, through such site and into such living body.

29. The appliance of claim 28, in further combination with:

such a thin elongate article that has means for conducting such substance lengthwise along at least a part of the elongate article.

30. The appliance of claim 29, wherein:

the conducting means comprise at least one groove formed in an exterior surface of the elongate article, for distribution of such substance to the interior of such living body.

31. The appliance of claim 39, wherein:

the conducting means comprise at least one internal passage within the elongate article, communicating with an exterior surface of the elongate article for distribution of such substance to the interior of such living body.

32. The appliance of claim 29, wherein:

the projecting means and conducting means comprise means for effectively transferring such substance from the reservoir into such living body along the elongate article.

33. The combination of claim 29, wherein:

the article is thin and elongate, and has generally spiral external grooving for conducting such substance from the dispensing appliance through such site and into such living body; and the projecting means comprise an outlet for the duct, within the shield, that is disposed and angled consistently with the grooving of the elongate article when a part of the article is disposed within the conduit, for projecting such substance from the attachment means into the grooving;

whereby the conduit projects such substance from the reservoir into and along the grooving, through such site and into such living body.

34. The appliance of claim 28, particularly for use in inserting or maintaining such thin elongate article within a urethra, such site being a urethral meatus; wherein:

the conduit is particularly sized to match a urethra;

whereby the conduit closely surrounds and encloses such thin elongate article that fits closely within such urethra; and whereby in use such substance is effectively applied along at least a part of the length of such urethra while such thin elongate article is positioned within such urethra.

35. The appliance of claim 33, particularly for use in inserting or maintaining the thin elongate article within a urethra, such site being a urethral meatus; wherein:

the conduit is particularly sized to match a urethra; and the article is particularly sized to fit closely within such urethra;

whereby in use such substance is effectively applied along at least a part of the length of such urethra while the thin elongate article is positioned within such urethra.

* * * * *

UNITED STATES PATENT AND TRADEMARK OFFICE
CERTIFICATE OF CORRECTION

PATENT NO. : 4,834,711

DATED : May 30, 1989

INVENTOR(S) : Albert R. Greenfeld and Jonathan I. Greenfeld

It is certified that error appears in the above-identified patent and that said Letters Patent is hereby corrected as shown below:

Cover page, item [19], "Greenfield et al. should read --Greenfeld et al.

Column 3, line 60, "catherers," should be --catheters,--.

Column 6, line 15, "he" should be --the--.

line 62, "user s" should be --user's--.

line 67, "said," should be --side,--.

Column 13, line 37, "shape" should be --shaped--.

Column 16, line 3, "39," should be --29,--.

Column 2, line 55, "infection-s" should be --infections--.

Column 2, line 65, "infection-s" should be --infections--.

Column 8, line 59, "applian-ce" should be --appliance--.

Column 11, line 26, "arrangemen-t" should be --arrangement--.

Signed and Sealed this

Twenty-sixth Day of June, 1990

Attest:

HARRY F. MANBECK, JR.

Attesting Officer

Commissioner of Patents and Trademarks